United States Patent
Watson, Jr.

(10) Patent No.: US 7,636,594 B2
(45) Date of Patent: Dec. 22, 2009

(54) INFANT WARMING AND SENSOR MAT

(75) Inventor: Richard L. Watson, Jr., McPherson, KS (US)

(73) Assignee: Maternus Partners, Ltd., San Antonio, TX (US)

( * ) Notice: Subject to any disclaimer, the term of this patent is extended or adjusted under 35 U.S.C. 154(b) by 0 days.

(21) Appl. No.: 10/571,450

(22) PCT Filed: Sep. 9, 2004

(86) PCT No.: PCT/US2004/029551

§ 371 (c)(1),
(2), (4) Date: Jan. 29, 2007

(87) PCT Pub. No.: WO2005/025406

PCT Pub. Date: Mar. 24, 2005

(65) Prior Publication Data

US 2007/0270670 A1 Nov. 22, 2007

(51) Int. Cl.
*A61B 5/1455* (2006.01)
*A61F 7/08* (2006.01)
(52) U.S. Cl. .............. 600/323; 600/310; 600/324; 607/107
(58) Field of Classification Search ............... 600/310, 600/322, 323, 324, 340; 607/104, 107, 108
See application file for complete search history.

(56) References Cited

U.S. PATENT DOCUMENTS

| | | | | | |
|---|---|---|---|---|---|
| 4,825,488 | A | * | 5/1989 | Bedford | 5/726 |
| 5,285,783 | A | * | 2/1994 | Secker | 600/323 |
| 5,675,852 | A | * | 10/1997 | Watkins | 5/726 |
| 5,887,304 | A | * | 3/1999 | von der Heyde | 5/726 |
| 6,336,237 | B1 | * | 1/2002 | Schmid | 5/726 |
| 6,596,016 | B1 | * | 7/2003 | Vreman et al. | 600/310 |

* cited by examiner

*Primary Examiner*—Eric F Winakur

(57) ABSTRACT

An infant warming and sensor mat for keeping a baby warm and monitoring the baby's haemoglobin oxygen saturation level ($SaO_2$) and heart rate. The mat preferably comprises a bottom layer of compressible padding material, a sensor layer comprising a plurality of light sources and light detectors, a cover layer having multiple openings, and an air layer between the sensor layer and cover layer. Warm air supplied to the air layer escapes through the openings in the cover to warm the baby. The light sources shine light of an appropriate wavelength onto the baby through the openings in the cover, and the light detectors sense the amount of light reflected back from the baby, which is indicative of $SaO_2$ level. Heart rate is also determined from the resulting periodic signal.

11 Claims, 1 Drawing Sheet

INFANT WARMING AND SENSOR MAT

BACKGROUND OF THE INVENTION

This invention relates generally to infant warming devices and infant vital signs monitors, and more particularly to a novel infant warming and sensor mat for keeping a baby warm and monitoring the baby's hemoglobin oxygen saturation level ($SaO_2$) and heart rate.

DETAILED DESCRIPTION OF THE PREFERRED EMBODIMENT

Figure 1:
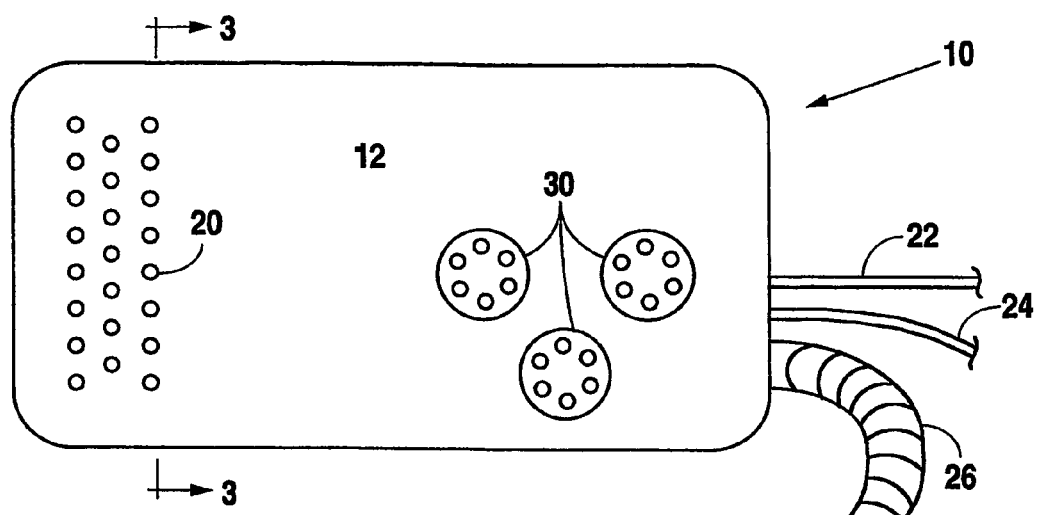
FIG. 1 is a top view of an infant warming and sensor mat in accordance with the present invention.
Figure 2:
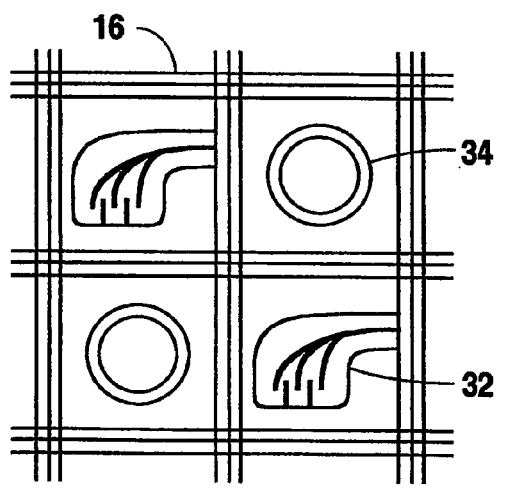
FIG. 2 is a detailed plan view of a portion of a sensor layer of the mat of FIG. 1.
Figure 3:
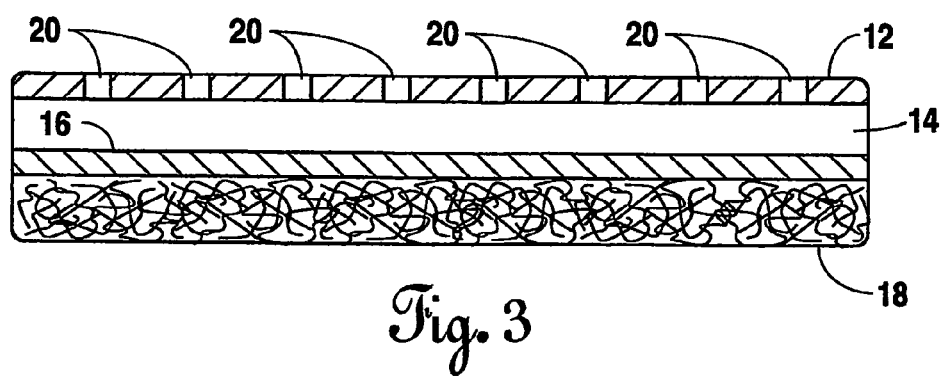
FIG. 3 is a sectional view taken along line 3-3 of FIG. 1.

As shown in FIGS. 1-3, the present invention is directed to a mat 10 on which a baby may be placed in order to keep the baby warm and to monitor the baby's hemoglobin oxygen saturation level ($SaO_2$) and heart rate. Mat 10 preferably comprises a bottom layer 18 of compressible padding material, a sensor layer 16 comprising a plurality of light sources 32 and light detectors 34, an air layer 14, and a cover layer 12 overlaying the other layers of the mat 10. The cover layer is anticipated to have multiple openings or fenestrations 20, extending through the cover layer, and which may be provided over all or a portion of cover layer 12.

Warm air from a heated air supply (not shown) is injected into the air layer 14 via an air hose 26 and is allowed to exit through the openings 20 in the cover 12 in order to keep the baby warm.

Figure 4:
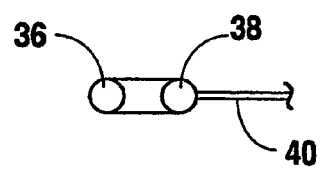
FIG. 4 is a schematic view of a combined light source and detector.

Sensor layer 16 preferably comprises a plurality of light sources 32 and light detectors 34 woven into a suitable fabric material. The light sources 32 and light detectors 34 may be arranged in groups, for example circular groups 30, but any desired shape is possible for such sensor groupings. As shown in FIG. 4, combination sensors having both a light source 36 and a light detector 38 serviced by signal line 40 may be used in sensor layer 16. The light sources 32, which may be supplied with light via light supply line 22, preferably emit red light of a single wavelength, which generally matches the wavelength of oxygenated hemoglobin. Alternatively, the light sources 32 may emit light containing a range of wavelengths, where the wavelength of oxygenated hemoglobin is included. The light is directed toward the openings 20 in the cover layer 12. Light supply line 22 may be a fiber optic cable, for example. Detectors 34 are in communication with a computer processor (not shown) via electrical line 24, or wirelessly.

When no baby is on the mat 10, the air layer 14 disperses the light sufficiently so that the amount of light emerging through the openings 20 in the cover 12 is not bothersome to medical personnel in the vicinity. When a baby is placed on the mat 10, the weight of the baby presses the cover 12 down toward the light sources 32 (i.e., the air layer gap 14 is substantially closed at the locations where the baby is lying), and the detectors 34 at those locations measure the amount of light that is reflected back from the baby through the openings 20 in the cover 12. As is known in the art, the amount of light reflected back from the baby is indicative of the baby's $SaO_2$ level. Additionally, because the baby's blood is pulsing through its blood vessels at a certain frequency, the signal received by the detectors 34 will be periodic, and the period of that signal is indicative of the baby's heart rate. The $SaO_2$ and heart rate calculations are preferably made by a computer processor (not shown) and the results displayed on a monitor (not shown) according to methods known in the art. Computer software known may preferably be employed to validate, cross-validate, accept and reject signals from multiple sensors for enhanced accuracy of the calculations and results to be displayed, as is familiar to those of skill in the art.

Although the foregoing specific details describe a preferred embodiment of this invention, persons reasonably skilled in the art will recognize that various changes may be made in the details of this invention without departing from the spirit and scope of the invention as defined in the appended claims. Therefore, it should be understood that this invention is not to be limited to the specific details shown and described herein.

I claim:

1. An infant warming and sensor mat comprising:
    a compressible layer for supporting the weight of an infant patient;
    a plurality of light sources; a sensor layer having a plurality of light detectors contained therein;
    a cover layer, wherein said cover layer overlays said sensor layer, and allows passage of light therethrough;
    at least one of said plurality of light sources being oriented to transmit light through said cover layer to a patient supported by said compressible layer;
    a computer processor in communication with said plurality of light detectors; and
    wherein, when a patient is placed upon said mat, at least one of said plurality of light sources and at least one of said plurality of light detectors cooperate with said computer processor to calculate a hemoglobin oxygen saturation level of the patient based on an amount of said light reflected from the patient.

2. The infant warming and sensor mat of claim 1 wherein said computer processor further calculates a heart rate of the patient.

3. The infant warming and sensor mat of claim 1, wherein light emitted by at least one of said plurality of light sources includes light having a range of wavelengths.

4. The infant warming and sensor mat of claim 1, wherein light emitted by at least one of said plurality of light sources has a single wavelength.

5. The infant warming and sensor mat of claim 1 further comprising a display monitor for displaying a representation of at least one of said hemoglobin oxygen saturation level and a heart rate of the patient.

6. An infant warming and sensor mat comprising: a sensor layer, wherein a plurality of light sources and a plurality of light detectors are contained therein; a cover layer, wherein said cover layer overlays said sensor layer and said cover layer has a plurality of openings therethrough; at least one of said plurality of light sources being oriented to shine light through at least one of said openings in said cover layer; a computer processor in communication with said plurality of light detectors; wherein, when a baby is placed upon said mat, at least one of said plurality of light sources and at least one of said plurality of light detectors cooperate with said computer processor to calculate a hemoglobin oxygen saturation level of the baby based on an amount of said light reflected from the baby; an air layer between said sensor layer and said cover layer; an air supply for providing warm air to said air layer, and wherein, when the baby is placed upon said mat, said warm air escapes through at least one of said plurality of openings to warm the baby.

7. An infant warming and sensor mat comprising: a padding layer; a sensor layer adjacent said padding layer, said sensor layer comprising a plurality of light sources and a plurality of light detectors; a cover layer having a plurality of openings therein; an air layer between said sensor layer and said cover layer, said plurality of light sources being oriented to shine light through said plurality of openings; an air supply for providing warm air to said air layer; and a computer processor in communication with said plurality of light detectors; wherein, when a baby is placed upon said mat, said warm air escapes through at least one of said plurality of openings to warm the baby, and at least one of said plurality of light sources and at least one of said plurality of light detectors cooperate with said computer processor to calculate a hemoglobin oxygen saturation level of the baby based on an amount of said light reflected from the baby.

8. The infant warming and sensor mat of claim 7 wherein said computer processor further calculates a heart rate of the baby.

9. The infant warming and sensor mat of claim 7, wherein light emitted by at least one of said plurality of light sources includes light having a range of wavelengths.

10. The infant warming and sensor mat of claim 7, wherein light emitted by at least one of said plurality of light sources has a single wavelength.

11. The infant warming and sensor mat of claim 7 further comprising a display monitor for displaying a representation of at least one of said hemoglobin oxygen saturation level and a heart rate of the baby.

* * * * *